United States Patent [19]

Lavanish

[11] 4,314,842
[45] Feb. 9, 1982

[54] HERBICIDAL SUBSTITUTED 1,3,4-THIADIAZOL-2-YL-4-HYDROXY-1-METHYL-2-IMIDAZOLIDINONES

[75] Inventor: Jerome M. Lavanish, Akron, Ohio

[73] Assignee: PPG Industries, Inc., Pittsburgh, Pa.

[21] Appl. No.: 195,146

[22] Filed: Oct. 8, 1980

Related U.S. Application Data

[63] Continuation-in-part of Ser. No. 65,694, Aug. 10, 1979, abandoned, and Ser. No. 79,277, Sep. 27, 1979, abandoned.

[51] Int. Cl.³ .................. A01N 43/82; C07D 417/04
[52] U.S. Cl. ........................................ 71/90; 562/512; 562/588; 562/598; 562/602; 548/137; 548/138; 548/140
[58] Field of Search ............................ 548/137; 71/90

[56] References Cited

U.S. PATENT DOCUMENTS

| | | | |
|---|---|---|---|
| 3,758,492 | 9/1973 | Metzger et al. | 548/137 |
| 3,759,939 | 9/1973 | Metzger et al. | 548/137 |
| 3,773,780 | 11/1973 | Metzger et al. | 548/137 |
| 3,849,432 | 11/1974 | Metzger et al. | 548/137 |
| 3,901,904 | 8/1975 | Krenzer | 548/137 |
| 3,901,905 | 8/1975 | Krenzer | 548/137 |
| 3,904,640 | 9/1975 | Krenzer | 548/137 |
| 3,920,674 | 11/1975 | Krenzer | 548/137 |
| 3,925,402 | 12/1975 | Krenzer | 548/137 |
| 3,964,895 | 6/1976 | Krenzer | 71/90 |
| 4,012,223 | 3/1977 | Krenzer | 71/90 |
| 4,023,957 | 5/1977 | Krenzer | 71/90 |
| 4,028,375 | 6/1977 | Krenzer | 548/137 |
| 4,036,848 | 7/1977 | Krenzer | 548/137 |
| 4,052,191 | 10/1977 | Krenzer | 71/90 |
| 4,093,443 | 6/1978 | Krenzer | 548/137 |
| 4,175,081 | 11/1979 | Driscoll | 548/141 |

*Primary Examiner*—Alton D. Rollins
*Attorney, Agent, or Firm*—Edward J. Whitfield

[57] ABSTRACT

This invention concerns certain substituted 1,3,4-thiadiazol-2-yl-4-hydroxy-1-methyl-2-imidazolidinones having herbicidal activity, their preparation, and the control of weeds therewith.

7 Claims, No Drawings

HERBICIDAL SUBSTITUTED 1,3,4-THIADIAZOL-2-YL-4-HYDROXY-1-METHYL-2-IMIDAZOLIDINONES

CROSS-REFERENCE TO RELATED APPLICATIONS

This application is a continuation-in-part of application Ser. No. 65,694, filed Aug. 10, 1979, and application Ser. No. 79,277, filed Sept. 27, 1979, both now abandoned.

FIELD OF THE INVENTION

This invention concerns certain substituted 1,3,4-thiadiazol-2-yl-4-hydroxy-1-methyl-2-imidazolidinones having herbicidal activity, their preparation, and the control of weeds therewith.

DESCRIPTION OF THE INVENTION

This invention concerns substituted 1,3,4-thiadiazol-2-yl-4-hydroxy-1-methyl-2-imidazolidinones represented by the formula:

$$R-X-\underset{R^2}{\underset{|}{\overset{R^1}{\underset{|}{C}}}}-\underset{N-N}{\overset{S}{\diagdown}}-N\underset{OH}{\overset{\overset{O}{\overset{\|}{C}}}{\diagup}}N-CH_3$$

wherein:
R is alkyl containing up to 4 carbon atoms;
$R^1$ is hydrogen or alkyl containing up to 4 carbon atoms;
$R^2$ is hydrogen, alkyl or haloalkyl containing up to 4 carbon atoms, alkenyl containing up to 3 carbon atoms, or alkynyl containing up to 3 carbon atoms; and
X is oxygen or sulfur.

Exemplary of alkyl groups represented in the above formula are methyl, ethyl, n-propyl, isopropyl, n-butyl, t-butyl, and isobutyl. Of the haloalkyl groups, chloro- or bromoalkyl are preferred, some examples of which are chloromethyl, bromomethyl, 2-chloroethyl, 2-bromoethyl, and the like. Ethenyl and propenyl are exemplary of alkenyl groups whereas ethynyl and propynyl are representative of alkynyl groups.

The compounds 3-[5-(1-methoxyethyl)-1,3,4-thiadiazol-2-yl]-4-hydroxy-1-methyl-2-imidazolidinone, 3-[5-(1-methoxy-1-methylethyl)-1,3,4-thiadiazol-2-yl]-4-hydroxy-1-methyl-2-imidazolidinone, 3-[5-(1-methylethoxy)ethyl)-1,3,4-thiadiazol-2-yl]-4-hydroxy-1-methyl-2-imidazolidinone, 3-[5-(1-methylthio-1-methylethyl)-1,3,4-thiadiazol-2-yl]-4-hydroxy-1-methyl-2-imidazolidinone, and 3-(5-methoxymethyl-1,3,4-thiadiazol-2-yl)-4-hydroxy-1-methyl-2-imidazlidinone have been found effective in controlling a variety of common weed species when applied either pre- or postemergent and it is believed that other compounds within the scope of the above formula would also exhibit herbicidal activity in accordance with this invention. Compounds wherein $R^2$ is alkyl and X is oxygen are particularly preferred.

It is, of course, to be understood that the stereo and optical isomers of compounds represented by the above formula are within the scope of this invention.

The compounds of this invention are typically synthesized in a five-stage reaction using techniques familiar to the art. Generally speaking, in the first stage, an alkali metal salt of an appropriately substituted alcohol (or thiol) is reacted with an appropriately substituted α-halo alkanoic ester to form a carboxylic acid represented by the formula:

$$R-X-\underset{R^2}{\underset{|}{\overset{R^1}{\underset{|}{C}}}}-\overset{O}{\overset{\|}{C}}-OH$$

wherein R, $R^1$, $R^2$, and X are as previously defined. The carboxylic acid is then reacted with an equimolar amount of thiosemicarbazide in the presence of excess phosphorous oxychloride yielding a 5-substituted-2-amino-1,3,4-thiadiazole, which latter compound is phosgenated to the corresponding isocyanate dimer. The isocyanate dimer is refluxed with an equivalent amount of methylaminoacetaldehyde dimethyl acetal to form the acetal urea which is then hydrolyzed to form the compounds of this invention.

The following Examples I through IV are illustrative of the synthesis of certain specific substituted 1,3,4-thiadiazol-2-yl-4-hydroxy-1-methyl-2-imidazolidinone compounds of this invention.

EXAMPLE I

The following examples illustrate the synthesis of the compounds described herein.

Synthesis of 3-[5-(1-methoxyethyl)-1,3,4-thiadiazol-2-yl]-4-hydroxy-1-methyl-2-imidazolidinone a. Formation of 2-methoxypropanoic acid A two liter flask equipped with a paddle stirrer, thermometer, condenser and nitrogen bubbler was charged with one liter of absolute methanol. Sodium metal (23.0 grams) was slowly added, when all of the metal was dissolved, the solution was cooled and starting at 8° C., 190 grams (1.05 mole) of ethyl 2-bromopropionate was added dropwise over a 55-minute period, the final temperature being 2° C. The solution was stirred for 45 minutes with ice bath cooling, then 250 milliliters of waters and 42 grams of sodium hydroxide pellets were added and the reaction mixture was stirred for an additional 75 minutes, while the temperature rose to 20° C. The reaction mixture was distilled at 90° C. to remove the methanol, then acidified with 85% phosphoric acid and extracted twice with 200 milliliters of chloroform (CHCl₃). The extracts were combined and dried over anhydrous magnesium sulfate (MgSO₄), filtered and then topped on a roto-vac at 50° C. to yield 81.1 grams of a colorless liquid of 2-methoxypropanoic acid.

b. Formation of 5-(1-methoxyethyl)-2-amino-1,3,4-thiadiazole

A 150 milliliter, 3-neck flask fitted with a Claisen adaptor, paddle stirrer, thermometer, an addition funnel and condenser was charged with 10.5 grams (0.10 mole) of 2-methoxypropanoic acid, prepared above, (9.1 grams, 0.10 mole) of thiosemicarbazide and 50 milliliters of dioxane. The slurry was heated to 90° C. and the addition funnel was charged with phosphorous oxychloride (POCl₃). The POCl₃ (16.9 grams, 0.11 mole) was slowly added (for 23 minutes) while maintaining the temperature within 85°–95° C. The resulting mixture was refluxed for 60 minutes and topped with a water aspirator to yield a gooey residue. Seventy-five (75) milliliters of water was added and 50% solution of NaOH was also added until the pH of the solution was 10; an aqueous phase formed. The mixture was placed in a continuous diethylether extractor and extracted for 150 minutes.

The diethylether extract was dried over anhydrous magnesium sulfate (MgSO4), filtered, and some white crystals formed. The extract was topped on a roto-vac at 70° C. to yield 7.0 grams of a white solid. The extractor was recharged with diethylether and after a 16 hour extraction, the diethylether solution was topped on a roto-vac to yield another 6.3 grams of a white solid. The white solids were combined and recrystallized from ethanol/chloroform to yield 8.6 grams of pale yellow crystals of 5-(1-methoxyethyl)-2-amino-1,3,4-thiadiazole. (Melting point 155°-159° C.).

c. Formation of 5-[1-methoxyethyl]-1,3,4-thiadiazol-2-yl isocyanate dimer

A 500 milliliter, 3-neck flask equipped with a magnetic stirrer, thermometer, dry ice condenser/drying tube and inlet from a phosgene (COCl2) tank via a calibrated rotameter was charged with 100 milliliters of ethyl acetate saturated with phosgene at 20° C. An additional 100 milliliters of ethylacetate was added; 7.9 grams of 5-(1-methoxyethyl)-2-amino-1,3,4-thiadiazole (prepared above) was added at a temperature from 0° C. to room temperature and a gooey oil formed. The resulting mixture was stirred for 17 hours and then the flask was purged with argon until no COCl2 was detected. The solution was filtered to yield a yellow cloudy solution which was topped 70° C. on a roto-vac to form 8.4 grams of a yellow viscous oil of 5-(1-methoxyethyl)-1,3,4-thiadiazol-2-yl isocyanate dimer.

d. Formation of 3-[5-(1-methoxyethyl)-1,3,4-thiadiazol-2-yl]-1-methyl-1-(2,2-dimethoxyethyl)urea At ambient temperatures, 5.4 grams (0.045 mole) of methylaminoacetaldehyde dimethylacetal was slowly added to a 50 milliliter benzene solution containing 8.4 grams (0.045 equivalents) of the 5-(1-methoxyethyl)-1,3,4-thiadiazol-2-yl isocyanate dimer (prepared above). The resulting solution was refluxed for 20 minutes; hexane was added resulting in the formation of an oil, the mixture was topped on a roto-vac at 70° C. to 13.2 grams of a hazy viscous oil which was dissolved in diethylether, and filtered. The diethylether solution was topped on a roto-vac at 70° C. to yield 12.9 grams of a red oil of 3-[5-(1-methoxyethyl)-1,3,4-thiadiazol-2-yl]-1-methyl-1-(2,2-dimethoxyethyl)urea.

e. Synthesis of 3-[5-(1-methoxyethyl)-1,3,4-thiadiazol-2-yl]-1-methyl-4-hydroxy-2-imidazolidinone A solution containing 4.2 grams of the 3-[5-1-methoxyethyl)-1,3,4-thiadiazol-2-yl]-1-methyl-(2,2,-dimethoxyethyl)urea (prepared above) in 150 milliliters of water and 1.5 milliliters of concentrated hydrochloric acid (HCl) was refluxed for 20 minutes, and the aqueous phase was extracted three times with 50 milliliters of chloroform (CHCl3). The 150 milliliter chloroform extract was dried over anhydrous MgSO4, filtered and topped on a roto-vac at 70° C. to yield 2.9 grams of a yellow viscous oil of 3-[5-(1-methoxyethyl)-1,3,4-thiadiazol-2-yl]-1-methyl-4-hydroxy-2-imidazolidinone with the following:

IR spectra: C=O band at 1720 cm$^{-1}$, broad N—H band at 3300 $^{-1}$cm.

NMR: (CDCl3) 6.62δ (br. singlet 1H), 6.17δ (mult., 1H), 4.69δ (quartet, 1H), 3.90δ (mult., 5H), 3.50δ (mult., 5H), 3.32δ (sing., 5H), 2.91δ (singlet, 3H), 1.53δ (doublet, 3H).

A second preparation of the above compound gave a crude oily product which produced crystals from ether/chloroform/hexane, m.p. 85°–91° C.

EXAMPLE II

3-[5-(1-(1-methylethoxy)ethyl]-1,3,4-thiadiazol-2-yl]-4-hydroxy-1-methyl-2-imidazolidinone a. Formation of 2-(1-methylethoxy)propanoic acid

A 500 milliliter, 3-neck flask equipped with a magnetic stirrer, thermometer, addition funnel, condenser and nitrogen bubbler was charged with 250 milliliters of dry isopropyl alcohol. Sodium metal (7.1 grams, 0.31 mole) in small pieces was added and the solution was heated to reflux to complete the reaction. After cooling to 60° C., 54.3 grams (0.30 mole) of ethyl 2-bromopropionate in 50 milliliters of isopropanol was added dropwise over a 20 minute period, and then the solution was refluxed for 2 hours, and left standing overnight. One hundred fifty (150) milliliters of water and 13.0 grams of sodium hydroxide pellets were added and then the mixture was distilled at 90° C., then cooled in an ice bath and acidified to pH2 with concentrated hydrochloric acid. The oil phase which formed was extracted with 150 milliliters of dichloromethane, CH2Cl2, and the extract was dried over anhydrous magnesium sulfate, filtered and topped on a roto-vac at 70° C. to yield 27.8 grams of a pale yellow viscous liquid of 2-(1-methylethoxy)propanoic acid.

b. Formation of 5-[1-(1-methylethoxy)ethyl]-2-amino-1,3,4-thiadiazole

A 150 milliliter, 3-neck flask equipped with a Claisen adaptor, paddle stirrer, thermometer, addition funnel and condenser was charged with 7.9 grams (0.060 mole) of 2-(1-methylethoxy)propanoic acid, (prepared above (5.5 grams, 0.060 mole) of thiosemicarbazide and 50 milliliters of dioxane. The slurry was heated to 95° C. and the addition funnel was charged with phosphorous oxychloride (POCl3). The POCl3 (10.1 grams, 0.066 mole) was slowly added (for 17 minutes) while maintaining the temperature within 85°-95° C. The reaction mixture was refluxed for 24 minutes, topped with a water aspirator to remove volatiles (HCl, POCl3 and some dioxane), leaving a residue to which 50 milliliters of water was added and a 50% solution of NaOH until the pH of the solution was 10. A two phase system formed, which was charged into a continuous diethylether extractor and extracted for 17 hours. The diethylether extract was topped on a roto-vac at 70° C. to yield 10.2 grams of white crystals which were recrystallized from the minimum amount of carbon tetrachloride/ethanol solution to yield white platelets. They were filtered off and air dried to yield 8.1 grams of white platelets of 5-[1-(1-methylethoxy)ethyl]-2-amino-1,3,4-thiadiazole, (melting point 129°-135° C.).

c. Formation of 5-[1-(1-methylethoxy)ethyl]-1,3-4-thiadiazol-2-yl isocyanate dimer A 200 milliliter, 3-neck flask equipped with a magnetic stirrer, thermometer, dry ice condenser/drying tube and inlet from a phosgene ($COCl_2$) tank via a calibrated rotometer was charged with 50 milliliters of ethyl acetate which was saturated with phosgene at 20° C. An additional 100 milliliters of ethyl acetate was added; (8.1 grams) of 5-[1-(1-methylethoxy)ethyl]-2-amino-1,3,4-thiadiazole (prepared above) was added at 20° C. The resulting solution was stirred overnight at room temperature, and the flask was purged with argon until no $COCl_2$ was detected. The cloudy solution was filtered to yield a solution which contained 5-[1-(1-methylethoxy)ethyl]-1,3,4-thiadiazol-2-yl isocyanate dimer.

d. Formation of 3-[5-[1-(1-methylethoxy)ethyl]-1,3,4-thiadiazol-2-yl]-1-methyl-1-(2,2-dimethoxyethyl)urea Methylaminoacetaldehyde dimethylacetal (5.6 grams, 0.047 mole) was added dropwise to the 150 milliliter ethyl acetate solution containing (0.047 mole) of the 5-[1-(1-methylethoxy)ethyl]-1,3,4-thiadiazol-2-yl isocyanate dimer (prepared above) and the resulting solution was heated to reflux, cooled and hexane was added and the resulting solution was placed in a refrigerator and topped on a roto-vac at 70° C. to yield 14.0 grams of an orange oil of 3-[5-[1-(1-methylethoxy)ethyl]-1,3,4-thiadiazol-2-yl]-1-methyl-1-(2,2-dimethoxyethyl)urea.

e. Synthesis of 3-[5-[1-(1-methylethoxy)ethyl]-1,3,4-thiadiazol-2-yl]-1-methyl-4-hydroxy-2-imidazolidinone A solution containing 4.2 grams of the 3-[5-[1-(2-methylethoxy) ethyl]-1,3,4-thiadiazol-2-yl]-1-methyl-(2,2-dimethoxyethyl)urea (prepared above), 150 milliliters of water and 1.5 milliliters of concentrated hydrochloric acid (HCl) was refluxed for 15 minutes, then cooled and extracted twice with 50 milliliters of chloroform. The chloroform solution was dried over anhydrous magnesium sulfate ($MgSO_4$), filtered, and topped on a roto-vac at 70° C. to yield 3.5 grams of a yellow oil which was dissolved in diethylether and seeded with crystals of Example Id. and allowed to crystallize overnight. White crystals formed which were removed by suction filter and then dried in a vacuum oven at 80° C. to yield 1.6 grams of white crystals of 3-[5-[1-(1-methylethoxy)ethyl]-1,3,4-thiadiazol-2-yl]-1-methyl-4-hydroxy-2-imidazolidinone. (Melting point 106°–108° C.).

EXAMPLE III
Synthesis of 3-[5-(1-methoxy-1-methylethyl)-1,3,4-thiadiazol-2-yl]-4-hydroxy-1-methyl-2-imidazolidinone a. Formation of 2-methyl-2-methoxypropanoic acid

A three liter flask equipped with a paddle stirrer, thermometer, condenser and cooled in an ice bath, was charged with one liter of methanol and 250 milliliters of water and 8.00 moles of 86% potassium hydroxide (KOH) pellets. The solution was stirred until all of the KOH was dissolved and 429 grams (2.00 mole) of 1,1,1-trichloro-2-methyl-2-propanol dihydrate dissolved in 500 milliliters of methanol was added slowly over a 3-hour period with ice bath cooling. The solution was stirred while allowing to warm slowly to room temperature and then refluxed for 135 minutes, then cooled. The reaction solution was suction filtered, washed with methanol and then topped with a roto-vac to 200 milliliters of solution, and then acidified with 85% phosphoric acid (while adding sufficient water to keep the mixture fluid), filtered and the filtrate extracted four times each with 250 milliliters of diethylether. The extracts were combined and dried over anhydrous magnesium sulfate ($MgSO_4$), filtered and then topped on a roto-vac at 60° C. to yield 161 grams of a colorless liquid containing 2-methyl-2-methoxypropanoic acid, which was vacuum distilled at 8 mm Hg pressure, and the fractions from 78° to 82° C. were collected.

b. Formation of 5-(1-methoxy-1-methylethyl)-2-amino-1,3,4-thiadiazole

Into a 150 milliliter, 3-neck flask equipped with a Claisen adaptor, paddle stirrer, thermometer, addition funnel and condenser were charged 7.1 grams (0.060 mole) of 2-methyl-2-methoxypropanoic acid, prepared above, (5.5 grams, 0.060 mole) of thiosemicarbazide and 50 milliliters of dry dioxane. The slurry was heated to 85° C. and the addition funnel was charged with phosphorous oxychloride ($POCl_3$). The $POCl_3$ (10.1 grams, 0.066 mole) was slowly added (for 20 minutes) while maintaining the temperature within 85°–95° C. The resulting suspension was refluxed for 1 hour and topped slightly with a water aspirator and then cooled. Fifty (50) milliliters of water was added and 50% solution of NaOH was also added until the pH of the solution was 10; an aqueous phase formed. The mixture was placed in a continuous diethylether extractor and extracted for 16 hours.

The diethylether extract was dried over anhydrous magnesium sulfate ($MgSO_4$), filtered and topped on a roto-vac at 70° C. to yield 5.6 grams of a pale yellow solid. The pale yellow solid was recrystallized from ethanol/chloroform/hexane, and filtered and dried in a vacuum oven to yield 2.2 grams of white crystals of 5-(1-methoxy-1-methylethyl)-2-amino-1,3,4-thiadiazole with a melting point of 115°–150° C.

A second run was made and the white solid crystals, 4.65 grams from the extract was combined with the first run crystals, the resulting mixture was purified by high pressure liquid chromatography using silica gel and acetone. The fraction was topped on a roto-vac to give 2.8 grams of an ivory residue of 5-(1-methoxy-1-methylethyl)-2-amino-1,3,4-thiadiazole, m.p. 143°–155° C. and Mass spectra—m/e at 173.

c. Formation of 5-[1-methoxy-1-methylethyl]-1,3,4-thiadiazol-2-yl isocyanate dimer A 500 milliliter, 3-neck flask equipped with a magnetic stirrer, thermometer, dry ice condenser/drying tube and inlet from a phosgene ($COCl_2$) tank via a calibrated rotometer was charged with 50 milliliters of ethylacetate saturated with phosgene at 20° C. An additional 50 milliliters of ethylacetate was added; 2.8 grams of 5-(1-methoxy-1-methylethyl)-2-amino-1,3,4-thiadiazole (prepared above) at a temperature of 0° C. was added. The resulting mixture was stirred for 17 hours at room temperature and then the flask was purged with argon until no $COCl_2$ was detected. The solution was filtered to yield a solution which contained about 0.008 moles of 5-[1-methoxy-1-methylethyl]-1,3,4-thiadiazol-2-yl isocyanate dimer.

d. Formation of 3-[5-(1-methoxy-1-methylethyl)-1,3,4-thiadiazol-2-yl]-1-methyl-1-(2,2-dimethoxyethyl)urea At ambient temperatures, 1.9 grams (0.016 mole) of methylaminoacetaldehyde dimethylacetal was added to the solution containing 0.008 mole of the 5-[1-methoxy-1-methylethyl]-1,3,4-thiadiazol-2-yl isocyanate dimer (prepared above). The resulting solution was heated to reflux, cooled and topped on a roto-vac at 70° C. to yield 4.9 grams of a yellow oil containing 3-[5-(1-methoxy-1-methylethyl)-1,3,4-thiadiazol-2-yl]-1-methyl-1-(2,2-dimethoxyethyl)urea.

e. Synthesis of 3-[5-(1-methoxy-1-methylethyl)-1,3,4-thiadiazol-2-yl]-1-methyl-4-hydroxy-2-imidazolidinone To the 4.9 grams of the 3-[5-[1-methoxy-1-methylethyl]-1,3,4-thiadiazol-2-yl]-1-methyl-(2,2-dimethoxyethyl)urea (prepared above) was added 150 milliliters of water and 1.5 milliliters of concentrated hydrochloric acid (HCl). The resulting solution was refluxed for 5 minutes, and the aqueous phase was extracted twice with 50 milliliters of chloroform (CHCl$_3$). The 100 milliliter chloroform extract was dried over anhydrous MgSO$_4$, filtered and topped on a roto-vac at 70° C. to yield 3.0 grams of a yellow oil of 3-[5-(1-methoxy-1-methylethyl)-1,3,4-thiadiazol-2-yl]-1-methyl-4-hydroxy-2-imidazolidinone with an IR spectra: C=O band at 1710 cm$^{-1}$, broad OH band at 3300 $-1^{cm}$.

EXAMPLE IV

Synthesis of 3-[5-(1-methylthio-1-methylethyl)-1,3,4-thiadiazol-2-yl]-hydroxy-1-methyl-2-imidazolidinone a. Formation of 1-methylthio-1-methylpropanoic acid

A 500 milliliter flask equipped with a stirrer, thermometer, condenser and nitrogen bubbler was charged with 200 milliliters of dry ethanol. Sodium metal (4.6 grams, 0.20 mole) was added in pieces and when it had all reacted, the solution was cooled in an ice bath and 16 grams (0.33 mole) of methyl mercaptan was added. Ethyl-bromoisobutyrate (39.0 grams, 0.20 mole) was added dropwise over a 38 minute period with formation of a white precipitate. The solution was then stirred overnight at room temperature after which nitrogen was bubbled through the solution until most of the mercaptan was removed. Sodium hydroxide pellets (9.0 grams) and 100 milliliters of water were then added to the solution and it was distilled to a 95° C. head temperature, cooled in an ice bath and made acidic to pH of 2.0 with concentrated hydrochloric acid. Water was added and the white precipitate was suction filtered off, and air dried to yield 19.4 grams of white crystals of 1-methylthio-1-methylpropanoic acid, having a melting point of 47°–49° C.

b. Formation of 5-(1-methylthio-1-methylethyl)-2-amino-1,3,4-thiadiazole

A 100 milliliter, 3-neck flask equipped with a Claisen adaptor, paddle stirrer, thermometer, addition funnel and condenser was charged with 9.4 grams (0.070 mole) of 1-methylthio-1-methylpropanoic acid, prepared above, (6.4 grams, 0.070 mole) of thiosemicarbazide and 30 milliliters of dry dioxane. The slurry was heated to 85° C. and the addition funnel was charged with phosphorous oxychloride (POCl$_3$). The POCl$_3$ (11.8 grams, 0.077 mole) was slowly added (for 10 minutes) while maintaining the temperature within 85°–95° C. The resulting suspension was heated for 15 minutes until it was very viscous, and topped slightly with a water aspirator and then cooled. Fifty (50) milliliters of water was added and 50 percent solution of NaOH was also added until the pH of the solution was 10; and a precipitate formed. It was suction filtered off, washed with water and air dried to yield 12.5 grams of crystals which were recrystallized from a cool basic ethanol/water mixture. The crystals were suction filtered off, washed with water and air dried to 8.3 grams of white crystals of 5-(1-methylthio-1-methylethyl)-2-amino-1,3,4-thiadiazole with a melting point of 195°–197° C.

c. Formation of 5-(1-methylthio-1-methylethyl)-1,3,4-thiadiazol-2-yl] isocyanate dimer A 300 milliliter, 3-neck flask equipped with a magnetic stirrer, thermometer, dry ice condenser/drying tube and inlet from a phosgene (COCl$_2$) tank via a calibrated rotometer was charged with 50 milliliters of ethyl acetate and then with 20 grams of phosgene. An additional 50 milliliters of ethylacetate and 6.6 grams (0.035 mole) of 5-(1-methylthio-1-methylethyl)-2-amino-1,3,4-thiadiazole (prepared above) at a temperature of 0° C. was added. The resulting mixture was stirred for 17 hours at room temperature and then the flask was purged with nitrogen until no COCl$_2$ was detected. The slurry was filtered, and the filter cake was dried in a vacuum oven to a m.p. of 161°–164° C., and the filtrate was topped on a roto-vac to yield more crystals with a m.p. of 161°–162° C., which were combined with the first crystals to yield 7.1 grams of 5-(1-methylthio-1-methylethyl)-1,3,4-thiadiazol-2-yl isocyanate dimer.

d. Formation of 3-[5-(1-methylthio-1-methylethyl)-1,3,4-thiadiazol-2-yl]-1-methyl-1-(2,2-dimethyoxyethyl)urea At ambient temperatures, 4.2 grams (0.035 mole) of methylaminoacetaldehyde dimethylacetal was added to 50 milliliters of benzene containing 7.1 grams (0.033 equivalents) of the 5-[1-methylthio-1-methylethyl]-1,3,4-thiadiazol-2-yl isocyanate dimer (prepared above). The resulting pink solution was heated to reflux, 100 milliliters of hexane was added, and the solution was cooled, filtered and topped on a roto-vac at 70° C. to yield 11.4 grams of a pale pink viscous oil of 3-[5-(1-methylthio-1-methylethyl)-1,3,4-thiadiazol-2-yl]-1-methyl-1-(2,2-dimethoxy-ethyl)urea.

e. Synthesis of 3-[5-(1-methylthio-1-methylethyl)-1,3,4-thiadiazol-2-yl]-1-methyl-4-hydroxy-2-imidazolidinone

1. First Preparation

To 4.0 grams of the 3-[5-(1-methylthio-1-methylethyl-1,3,4-thiadiazol-2-yl]-1-methyl-(2,2-dimethoxyethyl)urea (prepared above) was added 150 milliliters of water and 1.5 milliliters of concentrated hydrochloric acid (HCl). The resulting solution was refluxed for 5 minutes, cooled and the aqueous phase was extracted with 50 milliliters of chloroform (CHCl$_3$). The 50 milliliter chloroform extract was dried over anhydrous MgSO₄, filtered and topped on a roto-vac to yield 2.7 grams of a viscous oil containing 3[5-(1-methylthio--methylethyl)-1,3,4-thiadiazol-2-yl]-1-methyl-hydroxy-2-imidazolidinone. High pressure liquid chromatography was used to fractionate the oil, and the fractions were combined and allowed to stand. Ethylether/hexane was added to the oil with formation of crystals which were filtered off and air dried to yield 0.5 grams of ivory crystals of 3-[5-(1-methylthio-1-methylethyl)-1,3,4-thiadiazol-2-yl]-1-methyl-4-hydroxy-2-imidazolidinone, melting point 101°-104° C.

2. Second Preparation

A second preparation was made using 3.4 grams of 3-[5-(1-methylthio-1-methylethyl)-1,3,4-thiadiazol-2-yl]-1-methyl-(2,2-dimethoxyethyl)urea (prepared above), 150 milliliters of water and 1.5 milliliters of concentated hydrochloric acid (HCl). The resulting solution was refluxed for five minutes, cooled in ice, and extracted with 50 millilters of chloroform (CHCl₃). The extract was dried over magnesium sulfate (MgSO₄), filtered, topped on a roto-vac to 2.3 grams of an oily residue. Ethylether was added to the oily residue, and it was seeded with crystals from the first preparation and cooled in a refrigerator. The crystals which formed were removed by suction filtration and were air dried to 1.7 grams of white crystals of 3-[5-(1-methylthio-1-methylethyl)-1,3,4-thiadiazol-2-yl]-1-methyl-4-hydroxy-2-imidazolidinone with a melting point of 102°-105° C., IR (null) OH band at 3180 cm⁻¹ and C=O band at 1720 cm⁻¹

NMR (CDCl₃): 1.74δ (singlet, 6H), 195δ (singlet, 3H), 2.94 δ (singlet, 3H), 3.3-4.0 δ (multiplet, 2H), 5.90 δ (broad singlet) and 6.15 δ (multiplet), together 2H.

Although syntheses of certain compounds of this invention have been illustrated in some detail by the foregoing Examples, it is to be understood that any compound contemplated to be within the scope of this invention may be prepared by those skilled in the art by varying the choice of starting materials and using the illustrated techniques or any other suitable techniques.

The compounds of this invention have been found effective in regulating the growth of a variety of undesirable plants, i.e. weeds, when applied, in an herbicidally effective amount, to the growth medium prior to emergence of the weeds or to the weeds subsequent to emergence from the growth medium. The term "herbicidally effective amount" is that amount of compound or mixture of compounds required to so injure or damage weeds such that the weeds are incapable of recovering following application. The quantity of a particular compound or mixture of compounds applied in order to exhibit a satisfactory herbicidal effect may vary over a wide range and depends on a variety of factors such as, for example, hardiness of a particular weed species, extent of weed infestation, climatic conditions, soil conditions, method of application, and the like. Typically, as little as 0.2 or less pound per acre to 10 more pounds per acre of compound or mixtures of compounds may be required. Of course, the efficacy of a particular compound against a particular weed species may readily be determined by relatively straight forward laboratory or field testing in a manner well known to the art.

The compounds of this invention may be used as such or in formulation with agronomically acceptable adjuvants, inert carriers, other herbicides, or other commonly used agricultural compounds, for example, pesticides stabilizers, safeners, fertilizers, and the like. The compounds of this invention, whether or not in formulation with other agronomically acceptable materials, are typically applied in the form of dusts, granules, wettable powders, solutions, suspensions, aerosols, emulsions, dispersions or the like in a manner well known to the art. When formulated with other typically used agronomically acceptable materials, the amount of compound or compounds of this invention present in the formulation may vary over a wide range, for example, from about 0.05 to about 95 percent by weight on weight of formulation. Typically such formulations will contain from about 5 to about 75 percent by weight of compound or compounds of this invention.

The compounds of this invention have been found effective in controlling a variety of broadleaf and grassy weeds at application rates of two (2) pounds per acre or less pre- or postemergence while not significantly damaging desirable crops such as, for example, corn, wheat, rice, and soybeans. Exemplary of weeds that may be effectively controlled by the application of compounds of this invention are wild mustard (*Brassica kaber*); yellow foxtail (*Setaria glauca*); crabgrass (*Digitaria sanguinalis*); coffeeweed (Sesbanai spp.); velvetleaf (*Abutilon theophrasti*); johnsongrass (*Sorghum halepense*); barnyardgrass (*Echinochloa crusgalli*); jimsonweed (*Datura stramonium*); teaweed (*Sida spinosa*); tall morningglory (Roth); and the like.

The compounds prepared in accordance with Examples I and III were tested for herbicidal activity against the above-mentioned weed species under controlled laboratory conditions of light, temperature, and humidity. Seeds of selected weeds were planted in flats. Each compound was applied preemergent by spraying a solvent solution of the compound at the rate of two pounds per acre shortly after planting. The state of growth of the weeds was periodically observed and at the end of twenty-one days following application of the compound, many of the weeds were either killed or injured beyond recovery.

Although the invention has been described with specific references and specific details of embodiments thereof, it is to be understood that it is not intended to be so limited since changes and alterations therein may be made by those skilled in the art which are within the full intended scope of this invention as defined by the appended claims.

I claim:

1. Compounds represented by the formula:

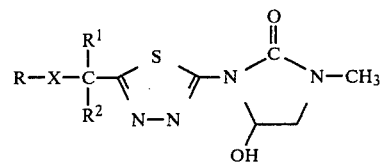

wherein:
R is alkyl containing up to 4 carbon atoms;
R¹ is hydrogen or alkyl containing up to 4 carbon atoms;
R² is hydrogen, alkyl or haloakyl containing up to 4 carbon atoms, alkenyl containing up to 3 carbon atoms, or alkynyl containing up to 3 carbon atoms; and
X is oxygen or sulfur.

2. The compound of claim 1 wherein X is oxygen.

3. The compound of claim 1 wherein $R^2$ is alkyl.

4. The compound of claim 1 wherein $R^1$ is hydrogen.

5. The compound of claim 1 wherein X is oxygen, R and $R^2$ are methyl, and $R^1$ is hydrogen.

6. The compound of claim 1 wherein X is oxygen and R, $R^1$, and $R^2$ are methyl.

7. In a method of controlling weed growth wherein a herbicidally effective amount of herbicide is either applied to the growth medium prior to emergence of the weeds or applied to the weed subsequent to emergence from the growth medium wherein the improvement resides in using as the herbicide a herbicidally effective amount of a compound or mixture of compounds defined in claim 1.

* * * * *